United States Patent [19]
Brunetti et al.

[11] Patent Number: 5,225,400
[45] Date of Patent: Jul. 6, 1993

[54] IMMUNOSTIMULATING PEPTIDES, A PROCESS FOR THEIR PREPARATION AND PHARMACEUTICAL COMPOSITIONS CONTAINING THEM

[75] Inventors: Brunetto Brunetti; Marco Prada, both of Milan, Italy

[73] Assignee: Ellem Industria Farmaceutica S.R.L., Milan, Italy

[21] Appl. No.: 785,026

[22] Filed: Oct. 30, 1991

Related U.S. Application Data

[63] Continuation-in-part of Ser. No. 384,327, Jul. 24, 1989, Pat. No. 5,079,231.

[30] Foreign Application Priority Data

Jul. 29, 1988 [IT] Italy ............................... 21556 A/88

[51] Int. Cl.$^5$ ..................... A61K 37/02; C07K 5/08
[52] U.S. Cl. ................................. 514/18; 530/331
[58] Field of Search ............... 530/330, 331; 514/11, 514/18

[56] References Cited

U.S. PATENT DOCUMENTS

| | | | |
|---|---|---|---|
| 4,428,938 | 1/1984 | Kisfaludy et al. | 530/331 |
| 4,505,853 | 3/1985 | Goldstein et al. | 530/330 |
| 4,650,788 | 3/1987 | Kessler et al. | 514/11 |
| 4,874,844 | 10/1989 | Brunetti et al. | 514/18 |

*Primary Examiner*—Merrell C. Cashion, Jr.
*Assistant Examiner*—S. G. Marshall
*Attorney, Agent, or Firm*—Bucknam and Archer

[57] ABSTRACT

Tripeptides having general formula II Glu-Lys-Arg in which: Glu is a glutamic acid residue, Lys is a lysine residue and Arg is an arginine residue are described. The aminoacids composing the tripeptides of the invention may be either of the natural, L-series or of the D-series or a racemic mixture of the two said series, but the aminoacids are preferably selected from the L-forms even though D- or DL aminoacids may also be considered. The invention refers also to the process for the preparation of said peptides as well as to their use as immunostimulant agents.

3 Claims, No Drawings

IMMUNOSTIMULATING PEPTIDES, A PROCESS FOR THEIR PREPARATION AND PHARMACEUTICAL COMPOSITIONS CONTAINING THEM

This application is a continuation-in-part of U.S. Ser. No. 384,327 filed Jul. 24, 1989 which has issued as U.S. Pat. No. 5,079,231 on Jan. 7, 1992, the subject matter of which is incorporated herein by reference.

The present invention relates to tripeptides having general formula II Glu-Lys-Arg in which: Glu is a glutamic acid residue, Lys is a lysine residue and Arg is an arginine residue.

The aminoacids composing the tripeptides of the invention may be either of the natural, L-series or of the D-series or a racemic mixture of the two said series, but the aminoacids are preferably selected from the L-forms even though D- or DL aminoacids may also be considered.

The invention refers also to the process for the preparation of said peptides as well as to their use as immunostimulant agents.

The tripeptide Arg-Ala-Arg is known from the Italian patent application no. 20027 A/86 of 9.04.1986: it is endowed with immunostimulating activity and it is able to enhance both the T-cells maturation and functional abilities.

Also the Arg-Lys-Glu tripeptide (splenotritin) corresponding to the 32-34 fragment of splenopoietin, a polypeptide hormone extracted from the bovine spleen and originally referred to as thymopoietin III because of its high affinity with thymopoietins I and II isolated from thymus, has immunostimulating properties, involving the maturation and functionality of T-lymphocytes (Italian patent application no. 20026 A/86 of 9.04.1986; Diezel W. et al.: Biomed. Biochim. Acta 45, 1349, 1986).

Similarly, the peptide Arg-Lys-Asp, differing from Arg-Lys-Glu only in the C-terminal aminoacidic residue, displays a similar behaviour (EP-A-0067425) as well as Arg-Gly-Asp, disclosed in the Italian patent application no. 21575 A/87 of 4.08.1987.

The peptides according to the invention proved to be active as immunostimulating agents, being effective in in vitro experimental models in promoting the maturation of murine immature T-lymphocytes and in enhancing the functionality of human T-cells. The peptides are capable of restoring the immune function in nude athymic mice, when administered for 5 days, 2 or 6 weeks by oral or i.p. route.

Like Arg-Ala-Arg and Arg-Lys-Glu, also the tripeptides of the present invention are stable to the in vitro simulated gastric juice.

Analogously to the two peptides above mentioned, the stability of which in the simulated gastric juice is related to the activity after oral administration, it has been demonstrated that also the peptides of the invention are endowed with immunostimulating activity both after oral administration and after parenteral administration.

This fact represents a remarkable advantage in the therapeutic use, with particular reference to the treatment of children and of other patients who do not tolerate the parenteral administration and also as a consequence of a better patient's compliance to the prescribed therapy.

According to what above described, the compounds of the invention have such features so as to make them particularly useful in the clinical practice for the therapy both of primary and secondary deficiencies.

The clinical utilities of immunostimulating compounds are described for instance in Immun. Lett. Vol. 16, 363, 1987, JAMA Vol. 258, 3005, 1987 and Drug Discovery and Development, Eds. Williams M. and Malick J. B., Humana 1987, p. 227, which are herein incorporated by reference.

For the intended use, the tripeptides of the invention may be administered either alone or in admixture with pharmaceutically acceptable carrier, in suitable pharmaceutical formulations which are a further object of the invention.

Examples of said formulations, which may be prepared using well known methods and excipients, such as those described in "Remington's Pharmaceutical Sciences Handbook", Mack Pub. Co., N.Y. U.S.A., are tablets, capsules, syrups, and the like for the oral administration whereas for the parenteral administration suitable forms are sterile solutions or suspensions in acceptable liquids, implants, etc. The preferred dosage form is a unit dose comprising from about 0.1 to about 500 mg of a tripeptide of formula II or the equivalent of a pharmaceutically acceptable salt thereof, such as acetate, hydrochloride, trifluoroacetate, sulfate salts.

The posology will depend on several factors such as type and seriousness of the pathologic conditions to be treated, patient's weight and sex, etc. and will be easily determined by the skilled practitioner. Generally one to four administrations a day will be prescribed.

The tripeptides II are prepared according to conventional methods, well known in peptide chemistry, such as solid state synthesis on resins.

The following non limitative examples are given as a further illustration of the invention.

EXAMPLE 1

GENERAL PROCEDURE FOR THE SOLID PHASE SYNTHESIS OF TRIPEPTIDES

1. Preparation of resins substituted with Boc-aminoacids

Chloromethylated polystyrene (1% crosslinked; 200-400 mesh) is swelled in dimethylformamide (DMF) (about 8-10 ml per g of resin), then treated with the Boc-aminoacid (1 mole per g of resin), followed by potassium fluoride (2 moles per g of resin). A small amount of solvent (5-10 ml) is then distilled off under vacuum after which the mixture is heated to 80°-100° C. for 16-18 hours. While cooling, the resin is filtered, washed with DMF, DMF:$H_2O$ 1:1, $H_2O$, ethanol, $CH_2Cl_2$ and methanol and then dried under vacuum. Substitution (calculated by the weight increase)=0.4-0.6 moles per g.

2. General synthetic procedure

The suitable amount of resin substituted with the C-terminal Boc-aminoacid in the desired sequence is sequentially treated at room temperature (20°-25° C.) with:

a) $CH_2Cl_2$
b) 50% $CF_3COOH:CH_2Cl_2$ (v/v)
c) 50% $CF_3COOH:CH_2Cl_2$ for 25'
d) $CH_2Cl_2$ (3 times)
e) isopropanol
f) 10% triethylamine:$CH_2Cl_2$ (v/v) (twice)
g) $CH_2Cl_2$
h) methanol (twice)
i) $CH_2Cl_2$ (twice)

The contact time for each treatment is 3–5 minutes except treatment c).

About 10–15 ml of solvent or of solvent reagent mixture are used per g of resin in each step.

j) The resin is stirred with a solution of the suitably protected last but one, Boc-aminoacid of the desired sequence 3 equivalents in $CH_2Cl_2$ Dicyclohexylcarbodiimide 3 equivalents is then added thereto in $CH_2Cl_2$. The reaction time is at least 2–4 hours and it may last overnight (16–18 hours).

The resin to which the peptide is bound is filtered and washed with $CH_2Cl_2$, methanol and $CH_2Cl_2$ and the synthesis completion is checked by the ninhydrin reaction. If the synthesis is incomplete, the same aminoacid is coupled again using half amounts of the reagents. The cycle is repeated for each aminoacid of the sequence, until this is completed.

After removal of the N-terminal Boc group, the resin to which the peptide is bound is carefully washed and dried under vacuum.

The peptide is detached from the resin and contemporaneously deprotected by treatment with anhydrous hydrofluoric acid (about 10 ml per g of resin) containing anisole (10% v/v) for 1 h at 0° C.

After evaporation of hydrofluoric acid under reduced pressure, the crude peptide is extracted by washing the resin with diluted aqueous acetic acid and the product is isolated by lyophilization.

3. Purification of the crude tripeptide

The crude tripeptides may be purified by reverse phase preparative HPLC using silanized silica with C18 chain with, for instance, a Waters Prep 500 instrument. Using a 5×30 cm column, equilibrated with the suitable aqueous buffer, such as aqueous 0,1% trifluoroacetic acid, the crude peptide (about 2 g) is applied on the column and eluted with a gradient containing increasing amounts of acetonitrile. The fractions are checked by analytical HPLC and those containing the product at the desired purity degree (>95%) are collected and lyophilized. Finally, the purified product is transformed in the desired salt by treatment with the desired salt form of an ion-exchange resin.

SYNTHETIC PROCEDURES

The following compounds have been synthesized and purified by the general synthetic procedure described in Example 1 of U.S. patent application Ser. No. 384,327:

1) GLU-LYS-ARG (Boc-$N^G$-tosyl-L-arginine=a; Boc-epsilon-2-chlorobenzyloxycarbonyl-L-lysine=b; Boc-gamma-benzyl-L-glutamic acid=c)
2) D-GLU-LYS-ARG (a; b; Boc-gamma-benzyl-D-glutamic acid=d)
3) GLU-D-LYS-ARG (a; Boc-epsilon-2-chlorobenzyloxycarbonyl-D-lysine=e; c)
4) GLU-LYS-D-ARG (Boc-$N^G$-tosyl-D-arginine=f; b; c)
5) D-GLU-D-LYS-ARG (a; e; d)
6) D-GLU-LYS-D-ARG (f; b; d)
7) GLU-D-LYS-D-ARG (f; e; c)
8) D-GLU-D-LYS-D-ARG (f; e; d)

CHEMICAL CHARACTERISTICS

All the compounds 1–8 exhibit a molecular weight of 431.5.

| Peptide | Appearance: white powders | |
|---|---|---|
| | Peptide content (%)* | Peptide purity** |
| 1 | 71.2 +/− 3% | >97% |
| 2 | 81.0 +/− 3% | >96% |
| 3 | 71.4 +/− 3% | >97% |
| 4 | 69.8 +/− 3% | >96% |
| 5 | 81.0 +/− 3% | >93% |
| 6 | 79.0 +/− 3% | >94% |
| 7 | 76.0 +/− 3% | >94% |
| 8 | 73.0 +/− 3% | >92% |

*Determined after acidic hydrolysis by OPA derivatization
**Determined by RP-HPLC

BIOLOGICAL CHARACTERISTICS

RNA synthesis in human T lymphocytes stimulated in vitro with phytohemagglutinin Human T lymphocytes incubated in vitro for 24 hrs in the presence of 0.5% phytohemagglutinin (PHA) and of different peptide concentrations, have been analyzed for the RNA synthesis by means of 3H-uridine labelling. The results show that the tripeptides of this invention are capable of stimulating RNA synthesis in PHA activated human lymphocytes.

| PEPTIDE | CONCENTRATION (mcg/ml) | 3-H URIDINE INCORPORATION (cpm) | |
|---|---|---|---|
| | | MEAN (+/− SE) | Δ % |
| — | 0.0 | 2756 (432) | — |
| 1 | 0.1 | 5344 (556)* | +94 |
| | 1.0 | 8235 (244)* | +199 |
| 2 | 0.1 | 4870 (546)* | +77 |
| | 1.0 | 7599 (377)* | +176 |
| 3 | 0.1 | 5531 (613)* | +101 |
| | 1.0 | 6985 (480)* | +153 |
| 4 | 0.1 | 4824 (318)* | +75 |
| | 1.0 | 7328 (523)* | +166 |
| 5 | 0.1 | 5258 (451)* | +91 |
| | 1.0 | 8139 (571)* | +195 |
| 6 | 0.1 | 5613 (384)* | +104 |
| | 1.0 | 8515 (564)* | +209 |
| 7 | 0.1 | 4829 (479)* | +75 |
| | 1.0 | 7033 (451)* | +155 |
| 8 | 0.1 | 5011 (345)* | +82 |
| | 1.0 | 7492 (466)* | +172 |

* = $p < 0.01$

In vitro synthesis of RNA by human lymphocytes activated with anti-T3 monoclonal antibody Human T lymphocytes activated in vitro with an activator more specific than PHA, i.e. the anti-T3 monoclonal antibody (1.56 ng/ml), were incubated with 1 mcg/ml of the tripeptides and the RNA synthesis was evaluated by means of the 3H-uridine incorporation.

As shown in the table, also in this case the peptides are capable of enhancing the RNA synthesis of the already activated cells.

| PEPTIDE | 3H-URIDINE INCORPORATION (cpm) | |
|---|---|---|
| | MEAN (+/− SE) | Δ % |
| — | 1263 (125) | — |
| 1 | 3626 (419)* | +187 |
| 2 | 2937 (263)* | +133 |
| 3 | 4127 (343)* | +227 |
| 4 | 3814 (338)* | +202 |
| 5 | 3822 (404)* | +203 |
| 6 | 3617 (414)* | +186 |
| 7 | 4382 (189)* | +247 |
| 8 | 3470 (316)* | +175 |

* = $p < 0.01$

In vitro DNA synthesis in human T lymphocytes stimulated by PHA

Human T lymphocytes incubated in vitro for 72 hrs in the presence of 0.5% PHA and different peptide concentrations were analyzed for the DNA synthesis (proliferation) by means of 3H-thymidine labelling. The results show that the peptides are able to stimulate the DNA synthesis.

| PEPTIDE | CONCENTRATION (mcg/ml) | 3H-THYMIDINE INCORPORATION (cpm) MEAN (+/− SE) | Δ % |
|---|---|---|---|
| — | 0.0 | 10338 (2987) | — |
| 1 | 0.1 | 19476 (6505) | +88 |
|   | 1.0 | 22915 (8326) | +122 |
| 2 | 0.1 | 18165 (4844) | +76 |
|   | 1.0 | 23990 (7012) | +132 |
| 3 | 0.1 | 18653 (7555) | +80 |
|   | 1.0 | 21547 (6897) | +108 |
| 4 | 0.1 | 17513 (5418) | +69 |
|   | 1.0 | 23280 (7676) | +125 |
| 5 | 0.1 | 18054 (6587) | +75 |
|   | 1.0 | 22366 (7074) | +116 |
| 6 | 0.1 | 16982 (4877) | +64 |
|   | 1.0 | 21242 (8656) | +105 |
| 7 | 0.1 | 19549 (6542) | +89 |
|   | 1.0 | 23125 (7395) | +124 |
| 8 | 0.1 | 18893 (7688) | +83 |
|   | 1.0 | 22871 (7134) | +121 |

The Table shows that the peptides under examination were capable of stimulating the ConA-induced proliferation.

| PEPTIDE | 3H-THYMIDINE INCORPORATION (cpm) MEAN (+/− SE) | Δ % |
|---|---|---|
| — | 67156 (6223) | — |
| 1 | 87318 (13455) | +30 |
| 2 | 88428 (12127) | +32 |
| 4 | 86525 (18646) | +29 |
| 8 | 89203 (14588) | +33 |

Stimulation of the in vitro IL-2 and IL-6 production by PHA activated cells

Human T lymphocytes have been incubated with PHA in the presence or in the absence of 1 mcg/ml of the peptides, for 24 hrs in the case of IL-2 and 72 h for IL-6. The supernatants were collected, filtered (0.2 μm) and assayed for the activity of IL-2 or IL-6 by addition at different concentrations to fresh T lymphocytes or to B cells coming from long term cultures. The proliferative activity of said cells, depending on the presence of the corresponding growth factor, has been evaluated by 3H-thymidine incorporation.

The Tables show that the peptides 1–8 are capable of stimulating IL-2 and IL-6 production.

| | IL-2 PRODUCTION (cpm) SUPERNATANT PERCENTAGE: | | | | | | | |
|---|---|---|---|---|---|---|---|---|
| | 3.1 | | 6.2 | | 12.5 | | 25 | |
| PEPT. | X +/− SE | Δ % | X +/− SE | Δ % | X +/− SE | Δ % | X +/− SE | Δ % |
| — | 2572 603 | — | 4741 710 | — | 12725 663 | — | 18554 3783 | — |
| 1 | 4346 67 | +69 | 16118 3922 | +240 | 26307 2190 | +107 | 32108 1611 | +73 |
| 2 | 3991 731 | +55 | 16727 1985 | +253 | 22281 4361* | +75 | 29783 2428 | +61 |
| 3 | 4452 206 | +73 | 15949 4421 | +236 | 25405 3377 | +100 | 31064 3965 | +67 |
| 6 | 4224 248 | +64 | 15602 2917 | +229 | 24867 2908 | +95 | 30185 3631 | +63 |
| 8 | 4568 553 | +78 | 15450 3547 | +226 | 23881 1658 | +88 | 30699 1252 | +65 |

| | IL-6 PRODUCTION (cpm) SUPERNATANT PERCENTAGE: | | | | | | | |
|---|---|---|---|---|---|---|---|---|
| | 3.1 | | 6.2 | | 12.5 | | 25 | |
| PEPT. | X +/− SE | Δ % | X +/− SE | Δ % | X +/− SE | Δ % | X +/− SE | Δ % |
| — | 2976 645 | — | 5765 1875 | — | 10187 3168 | — | 18846 2664 | — |
| 1 | 5113 1135 | +72 | 14078 6143 | +144 | 19977 5419 | +96 | 24966 3955 | +32 |
| 2 | 4473 1737 | +50 | 13024 4503 | +126 | 21915 7150 | +115 | 26271 2428 | +39 |
| 3 | 4983 939 | +67 | 15674 5395 | +172 | 20820 5188 | +104 | 26378 3104 | +40 |
| 6 | 4966 1399 | +67 | 13183 5868 | +129 | 21730 4967 | +113 | 25311 4123 | +34 |
| 8 | 4343 490 | +46 | 13341 4934 | +131 | 20137 6413 | +98 | 24673 4757 | +31 |

In vitro stimulation of ConA-induced proliferation

Peripheral blood mononuclear cells (PBMC), obtained from healthy volunteers, were incubated with ConA in order to evaluate the proliferation as labeled thymidine uptake. The peptides n. 1, 2, 4 and 8 were used at the concentration of 0.1 mcg/ml.

In vitro IL-2 production by ConA-activated human cells

PBMC obtained from healthy volunteers were incubated overnight with the peptides 1–8 and analyzed for IL-2 production by means of an ELISA test, by reading the plates after 30 or 60 min. The cells were activated with 10 mcg/ml of ConA; the peptides were used at the concentration of 1 mcg/ml.

The results show that these peptides are capable of increasing IL-2 production.

| PEPTIDE | IL-2 PRODUCTION AFTER: | | | |
|---|---|---|---|---|
| | 30 min | | 60 min | |
| | U/ml | Δ % | U/ml | Δ % |
| — | 1.5 | — | 1.5 | — |
| 1 | 2.4 | +60 | 1.7 | +13 |
| 2 | 2.5 | +67 | 1.8 | +20 |
| 3 | 2.2 | +47 | 1.8 | +20 |
| 4 | 2.3 | +53 | 1.7 | +13 |
| 5 | 2.0 | +33 | 1.9 | +27 |
| 6 | 2.4 | +60 | 1.8 | +20 |
| 7 | 2.3 | +53 | 1.8 | +20 |
| 8 | 2.2 | +47 | 1.9 | +27 |

Ex-vivo stimulation of mitogen-induced proliferation

The stimulation of mitogen-induced proliferation has been investigated by oral or i.p. administration of the peptides to nude athymic mice (body weight 28 g) at the daily dosage of 10 mcg/mouse for 5 days or 6 weeks.

The animals were sacrificed 24 h after the last treatment and the proliferation was determined as labeled thymidine uptake by the spleen cells.

As it can be seen from the following Tables, the in vivo administration of the peptides stimulates the ex-vivo determined mitogen-induced proliferation.

| MITOGEN | CONTROLS X +/− SE | PEPT.1 X +/− SE | Δ % | PEPT.2 X +/− SE | Δ % | PEPT.4 X +/− SE | Δ % | PEPT.8 X +/− SE | Δ % |
|---|---|---|---|---|---|---|---|---|---|
| MITOGEN-INDUCED PROLIFERATION IN NUDE MICE TREATED ORALLY FOR 5 DAYS WITH 10 mcg/mouse OF THE PEPTIDES (cpm) | | | | | | | | | |
| PHA % | | | | | | | | | |
| 0.000 | 398 / 54 | 891 / 148 | +124 | 693 / 86 | +74 | 706 / 212 | +77 | 973 / 69 | +144 |
| 0.125 | 372 / 47 | 714 / 144 | +92 | 713 / 33 | +92 | 802 / 117 | +116 | 1114 / 435 | +199 |
| 0.500 | 524 / 94 | 1645 / 64 | +214 | 1493 / 231 | +185 | 1526 / 99 | +191 | 1921 / 214 | +267 |
| 2.000 | 3086 / 1476 | 3708 / 68 | +20 | 4015 / 201 | +30 | 3537 / 80 | +15 | 5144 / 1462 | +67 |
| PWM % | | | | | | | | | |
| 0.000 | 583 / 166 | 908 / 68 | +56 | 874 / 155 | +50 | 891 / 42 | +53 | 987 / 30 | +69 |
| 0.125 | 407 / 69 | 2296 / 101 | +464 | 1878 / 412 | +361 | 2051 / 265 | +404 | 2531 / 413 | +522 |
| 0.500 | 573 / 14 | 4673 / 821 | +716 | 4423 / 553 | +672 | 5690 / 771 | +893 | 6301 / 1092 | +1000 |
| 2.000 | 1133 / 487 | 5014 / 2655 | +343 | 5541 / 989 | +389 | 4838 / 1556 | +327 | 5979 / 1303 | +428 |
| ConA mcg/ml | | | | | | | | | |
| 0.000 | 371 / 40 | 914 / 27 | +146 | 1061 / 236 | +186 | 898 / 185 | +142 | 1048 / 405 | +182 |
| 0.312 | 417 / 98 | 4523 / 564 | +985 | 5146 / 164 | +1134 | 4805 / 1162 | +1052 | 5503 / 955 | +1220 |
| 0.625 | 478 / 74 | 10978 / 742 | +2197 | 11652 / 2197 | +2338 | 12356 / 1375 | +2485 | 13372 / 3849 | +2697 |
| 1.250 | 748 / 169 | 27895 / 2385 | +3629 | 29781 / 3518 | +3881 | 28171 / 2554 | +3666 | 31523 / 5395 | +4115 |
| MITOGEN-INDUCED PROLIFERATION IN NUDE MICE TREATED ORALLY FOR 6 WEEKS WITH 10 mcg/mouse OF THE PEPTIDES (cpm) | | | | | | | | | |
| PWM % | | | | | | | | | |
| 0.000 | 1256 / 190 | 4005 / 1142 | +219 | 3886 / 1169 | +209 | 4294 / 2202 | +242 | 4679 / 345 | +273 |
| 0.125 | 808 / 72 | 2397 / 318 | +197 | 2265 / 184 | +180 | 2236 / 370 | +177 | 2627 / 467 | +225 |
| 1.000 | 1223 / 638 | 2632 / 105 | +115 | 2923 / 427 | +139 | 2525 / 172 | +106 | 3495 / 645 | +186 |
| MITOGEN-INDUCED PROLIFERATION IN NUDE MICE TREATED I.P. FOR 6 WEEKS WITH 10 mcg/mouse OF THE PEPTIDES (cpm) | | | | | | | | | |
| PWM % | | | | | | | | | |
| 0.000 | 2088 / 200 | 2904 / 113 | +39 | 2785 / 308 | +33 | 2876 / 198 | +38 | 3495 / 373 | +67 |
| 0.125 | 2351 / 385 | 3338 / 1675 | +42 | 3621 / 1198 | +54 | 3496 / 1401 | +49 | 3827 / 1070 | +63 |
| 0.250 | 3018 / 127 | 4189 / 288 | +39 | 4005 / 291 | +33 | 4338 / 527 | +44 | 4471 / 274 | +48 |
| 0.500 | 2245 / 714 | 3648 / 406 | +62 | 3894 / 249 | +73 | 3721 / 345 | +66 | 4361 / 274 | +94 |

| MITOGEN | CONTROLS X +/− SE | PEPT.1 X +/− SE | Δ % | PEPT.2 X +/− SE | Δ % | PEPT.4 X +/− SE | Δ % | PEPT.8 X +/− SE | Δ % |
|---|---|---|---|---|---|---|---|---|---|
| 1.000 | 3339 425 | 3263 988 | −2 | 3461 1227 | +4 | 3365 964 | +1 | 3887 778 | +16 |
| 2.000 | 2621 464 | 2627 534 | 0 | 2789 531 | +6 | 2698 564 | +3 | 2978 293 | +14 |
| ConA mcg/ml | | | | | | | | | |
| 0.00 | 2165 394 | 2686 547 | +24 | 2747 406 | +27 | 2322 688 | +7 | 2617 415 | +21 |
| 0.25 | 2177 208 | 6671 328 | +206 | 7009 643 | +222 | 6768 219 | +211 | 7165 886 | +229 |
| 0.50 | 2284 186 | 10428 741 | +357 | 10656 1565 | +366 | 11549 653 | +406 | 13564 1480 | +493 |
| 1.00 | 3187 304 | 16870 1938 | +429 | 17337 949 | +444 | 16912 1399 | +431 | 19558 906 | +514 |
| 2.00 | 2707 733 | 9829 1104 | +263 | 10957 603 | +305 | 11654 1047 | +331 | 13472 1162 | +398 |
| 4.00 | 1827 276 | 2722 800 | +49 | 2974 898 | +63 | 2661 904 | +46 | 3386 1212 | +85 |

ACUTE TOXICITY

The tripeptides 1-8 of the invention have a LD50 higher than 1000 mg/kg i.p. in the mouse.

What is claimed is:

1. The tripeptide Glu-Lys-Arg or a pharmaceutically acceptable salt thereof wherein the aminoacids glutamic acid, lysine and arginine are of the D-, L- or DL series.

2. The tripeptide, according to claim 1 wherein said salt is the acetate, trifluoroacetate, sulfate, or hydrochloride salt.

3. A pharmaceutical composition having immunostimulating activity comprising as the active principle an effective amount of the tripeptide Glu-Lys-Arg or a pharmaceutically acceptable salt thereof in a mixture with an acceptable carrier.

* * * * *